United States Patent [19]

Adler et al.

[11] 4,120,262
[45] Oct. 17, 1978

[54] APPARATUS FOR TRANSFERRING A PLURALITY OF SMEARS

[75] Inventors: Stanford L. Adler, Monsey, N.Y.; Abraham Gordon, Teaneck, N.J.

[73] Assignee: Technicon Instruments Corporation, Tarrytown, N.Y.

[21] Appl. No.: 806,640

[22] Filed: Jun. 15, 1977

Related U.S. Application Data

[63] Continuation of Ser. No. 642,421, Dec. 19, 1975, abandoned.

[51] Int. Cl.² ............................................... B05C 1/02
[52] U.S. Cl. ................................. 118/642; 118/206; 118/257; 156/241
[58] Field of Search .................. 118/257, 206, 642; 427/2, 4; 156/237, 241; 8/3, 54.11

[56] References Cited

U.S. PATENT DOCUMENTS

| 3,629,036 | 12/1971 | Isaacson | 156/241 |
| 3,871,895 | 3/1975 | Adler | 118/257 X |

*Primary Examiner*—John P. McIntosh
*Attorney, Agent, or Firm*—S. P. Tedesco

[57] ABSTRACT

A method of transferring a substance adhering to the surface of a substrate to a receiving surface of a backing element which includes locating the substrate surface in juxtaposition with the receiving surface, supplying a transfer medium on the receiving surface in sufficient quantity to encapsulate the substance, joining the transfer medium on the backing element with a substance so as to encapsulate the substance within the transfer medium and removing the substrate to expose the encapsulated substance.

7 Claims, 7 Drawing Figures

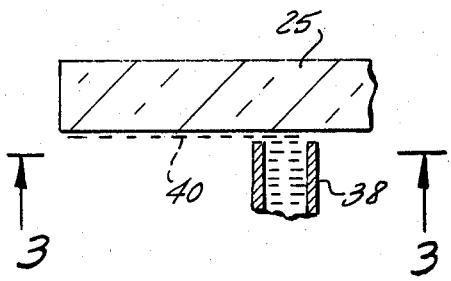
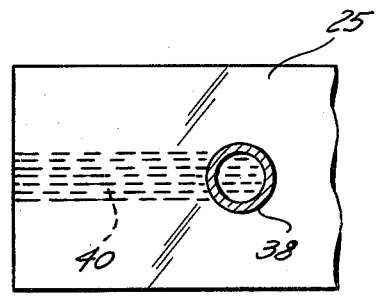
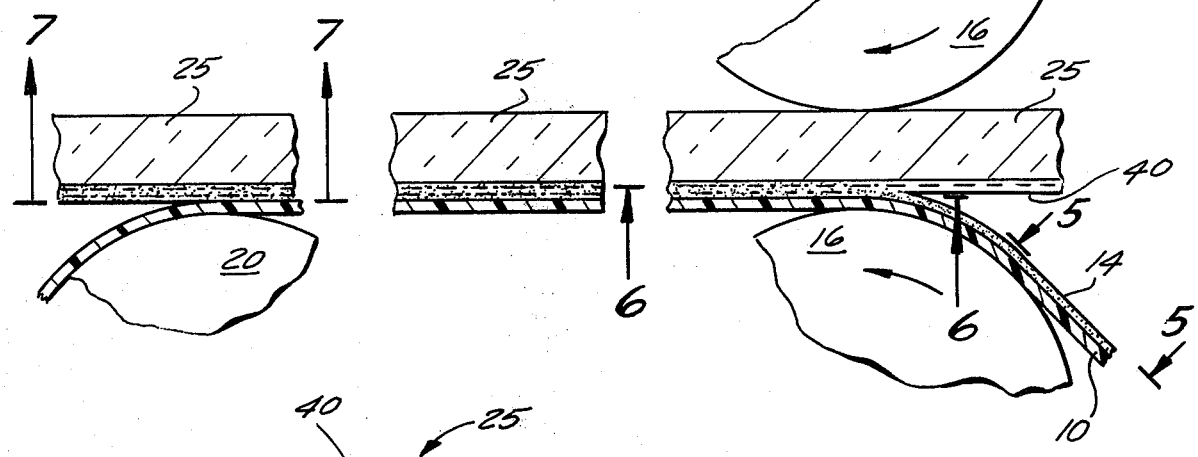
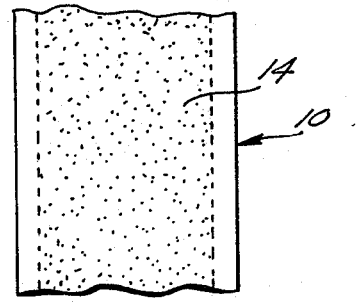
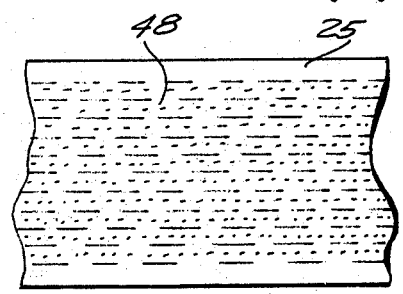

APPARATUS FOR TRANSFERRING A PLURALITY OF SMEARS

This is a continuation of application Ser. No. 642,421, filed Dec. 19, 1975, now abandoned.

BACKGROUND OF THE INVENTION

1. Field of the Invention

This invention relates to apparatus for transferring a dried, fixed and stained smear of a biological substance from a substrate to a backing element which provides a permanent mounting for the smear for examination of the smear under a microscope.

2. Prior Art

There is disclosed in Adler U.S. Pat. No. 3,871,895 apparatus and a method which may be automated for preparing a smear of a biological substance on a substrate. The smear may comprise a whole blood specimen or other type of cellular suspension. Such smears are useful for examination of the cellular material for diagnostic purposes.

That technique, which utilizes a ribbon element, may be characterized as including the steps of supporting the substrate element for movement, supporting the ribbon element for movement in close proximity to the substrate element at a sample-applying station, introducing a relatively small quantity of a biological liquid sample between the ribbon and substrate elements at the sample-applying station, spreading the sample across at least the central portion of the ribbon element, drawing the sample on the substrate element by moving one of the elements relatively to the other, and moving the ribbon element by advancing it to present a fresh portion thereof to the sample-applying station. In the form illustrated there by way of example, the substrate is a flexible tape and the patent details the manner in which such a smear-carrying tape should be at least temporarily assembled by manipulation with a microscope slide for examination under a microscope with the tape in place.

The present invention deals at least in part with the permanent mounting of a transferred smear on a microscope slide for such examination without the presence of a tape or the like.

SUMMARY OF THE INVENTION

One object of the invention is to provide a permanent microscope-ready backing for a biological smear transferred intact in fixed and stained condition from a substrate on which the smear was prepared.

Another object is to provide such a transferred smear which is encapsulated in a clear, scratch-resistant material which permeates the cellular matter of the smear and has an index of refraction which approaches that of the cellular matter. Such scratch-resistant material may be an adhesive fixed to the backing or may be the backing material itself which was previously softened in the appropriate smear-receiving area by the application of a solvent to a surface stratum of the backing.

There is provided an apparatus for transferring a biological substance smeared and dried on a surface of a substrate to a smear-receiving surface of a backing element which includes locating the substrate surface in juxtaposition with the receiving surface, supplying a transfer medium on the receiving surface in sufficient quantity to encapsulate the substance, joining the transfer medium on the backing element with a substance so as to encapsulate the substance within the transfer medium and removing the substrate to expose the encapsulated substance.

BRIEF DESCRIPTION OF THE DRAWINGS

In the drawings:

FIG. 2 is an enlarged fragmentary view in side elevation illustrating a portion of the apparatus of FIG. 1 in an operating condition;

FIG. 3 is a view taken on line 3—3 of FIG. 2;

FIG. 4 is a broken, fragmentary, side elevational view diagrammatically illustrating sequential functions of the apparatus of FIG. 1; and FIGS. 5, 6 and 7 are views taken on lines 5—5, 6—6 and 7—7, respectively, of FIG. 4.

DETAILED DESCRIPTION OF THE PREFERRED EMBODIMENTS

Figure 1:
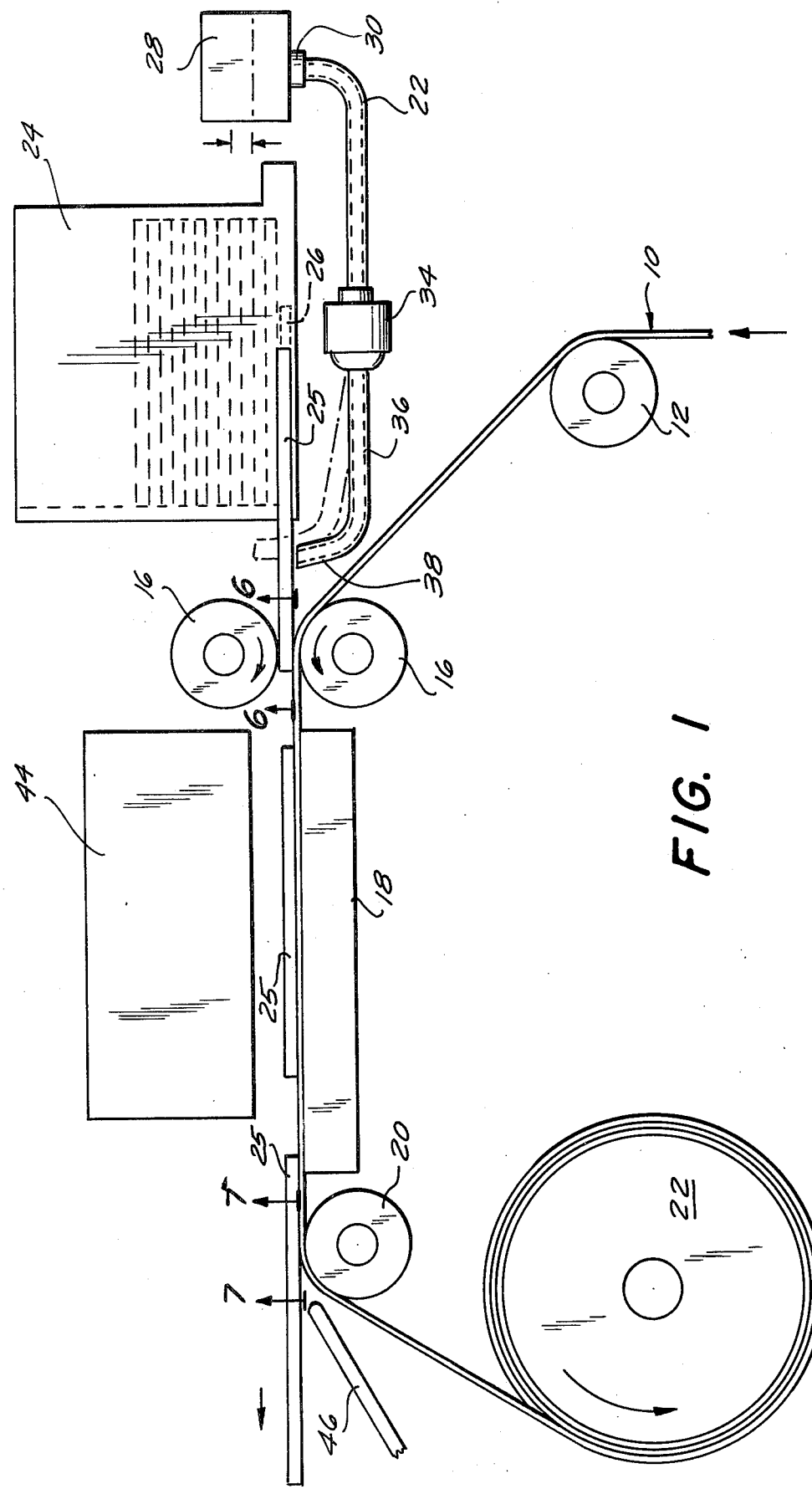
FIG. 1 is a fragmentary somewhat diagrammatic view in side elevation of apparatus embodying the invention.

There is disclosed in Adler U.S. Pat. No. 3,871,895 apparatus and a method for preparing a smear of a biological fluid substance on a substrate. In the illustrated form of that disclosure, a series of different blood samples are applied sequentially as smears in axially spaced condition along a common substrate in the form of a tape and the smears are fixed, stained and dried. While in that illustration the tape is shown as being cut into convenient sections each having a smear thereon, it will be evident that the tape may be collected on a take-up spool or fed directly into other apparatus for performing subsequent operations on the smears. Such apparatus for performing other operations on the smears is shown in FIG. 1 hereof wherein the substrate or tape issuing from a source, not shown, such as the apparatus of that patent for example, is trained over an idler roller 12. The substrate or tape 10 may be formed conveniently of Mylar resin, cellulose acetate, polyethylene or polypropylene for example. As best shown in FIGS. 4 and 5 one of a plurality of such smears axially spaced apart on the tape is indicated at 14. Such smears are located on the tape surface remote from the tape surface in contact with the roller 12. The tape 10 passes from the roller 12 to a position intermediate a pair of driven pinch rolls 16 and thence over a fixed platen 18 from which it is directed over an idler roller 20 and thence to a collection take-up spool 22 which is driven, preferably continuously, in the direction of the arrow.

The apparatus includes a stationary upright housing 24 open at the top and having four side walls and a bottom and holding in vertically stacked relation a supply of smear-receiving backing elements 25 which in the illustrated form are rigid and may take the form of microscope slides which may be fed by gravity to the bottom of the housing 24. The housing 24 has a dispensing opening in one side near the bottom and through which the slides 25 are dispensed one after another, separated by an interval of time, by a pusher 26 to a position intermediate the driven pinch rolls 16 which are biased together in a conventional manner, not shown. The rolls 16 sandwich the tape 10 and each slide 25 therebetween with the slide overlying a corresponding smear 14. Once free of the rolls 16, each slide 25 is carried by the traveling tape passing over the platen 18.

A transfer medium is required to transfer the smears 14 to the respective slides 25 without altering their morphological or stain characteristics. The medium is a substance producing adhesion between each smear and the corresponding slide which is greater than the affinity of the smear to the tape. Such a transfer medium may consist of a liquid adhesive applied between each smear and the corresponding slide and which is subsequently cured in a manner appropriate to the selected adhesive. Suitable adhesives will be discussed hereinafter. Alternatively, the transfer medium may be formed in situ on the underside of the corresponding slide structured of a suitable plastic material and consist of a solute in a tacky, semi-fluid state including plastic material derived from the slide and a suitable solvent. This transfer medium or solute is formed by applying such solvent to the underside of the slide. Inasmuch as it is necessary thereafter to dissipate or diffuse the solvent to harden the transfer medium, such diffusion of the solvent is characterized hereinafter in the appended claims, largely as a matter of convenience, as "curing" of the transfer medium.

By way of example, there is provided a fixed receptacle 28 for a supply of a liquid agent which may be the transfer medium including adhesive material in liquid form or which may be only a constituent of a transfer medium such as a liquid solvent. The receptacle 28 in practice is of substantial cross section, open at the top to the atmosphere, and has an outlet 30 at the bottom thereof coupled to one end of a rigid tube 32. The other end of the tube 32 is connected to the inlet of a fluid coupling 34 which has a conventional pivotal spring-biased outlet connected to the inlet end of a rigid tube 36 to bias the tube 36 from the full-line dispensing position thereof of FIG. 1 to the broken-line nondispensing position thereof. As shown, the tube 36 has an upwardly directed outlet position 38. In the nondispensing position of the tube 36, the outlet thereof is at the same horizontal level or higher than the liquid level with the receptacle 28. However, as a slide 25 is ejected from the housing 28 by the pusher 26, the slide contacts the outlet portion 38 of the tube and deflects it in a manner to lower it to the full-line position below such liquid level wherein liquid from the receptacle 28 flows through the outlet to dispense a relatively narrow band of such liquid 40 on the lower surface of the slide as the latter moves over the outlet in the manner best illustrated in FIGS. 2 and 3.

Each slide 25 with the applied liquid agent on the underside thereof is moved one after another into registry with the tape 10 in such phased relation to a corresponding smear on the tape that the slide is superimposed on the smear where the slide and the tape are brought together between the pinch rolls 16 before passing with the tape onto the platen in the same superimposed relationship. For example, the smears may be of a thickness of less than 0.0002 inch, a width of 0.5 inch and a length of 2.75 inches, while the slides 25 may be of any convenient thickness, a length of 3.0 inches and a width of 1.0 inch. As each slide 25 is drawn into intimate contact with the tape by the pinch rolls 16, the liquid 40 on the underside thereof spreads as a coating across the slide to the extent indicated in FIG. 6, a distance at least slightly greater than the width of the underlying smear 14. No pressure as such is required to transfer a smear 14 to a slide 25. The compressive force of the pinch rolls 16 need be only sufficient to spread the liquid 40 quickly in a thin, flat layer. On the aforementioned spreading of the liquid 40 by the pin rolls 16, the liquid permeates the smear 14 including cellular material thereof and encapsulates the smear. Such flow of the liquid 40 into a smear 14 is indicated in FIG. 4. Upon movement of the trailing edge of slide past the biased tube 36, the tube 36 is returned to the nondispensing position thereof.

As previously indicated, the appropriate curing of the transfer medium applied or formed on the underside of the slide will depend upon the nature of the selected transfer medium. One class of suitable transfer medium includes a cyanoacrylate monomer adhesive which is polymerizable within 10–60 seconds by surface-adsorbed basic catalysts, such as water, producing a thin, flat, transparent, hard mass strongly adhering to the slide, having a scratch-resistant surface and a refractive index approaching that of the cellular material of the smear, in which the smear is encapsulated and the cellular material thereof permeated by such adhesive. A second class of suitable transfer media includes an adhesive mixture of vinyl monomers or monomers and polymers, the polymerization of which is initiated by a photocatalyst such as benzoin, benzoin ethers, benzil or Michler's ketone and with or without addition of a polymerization accelerator such as N, N dimethyl aniline, when exposed to light of the appropriate wavelength, e.g. near ultraviolet when benzil is used, producing a mass such as characterized above with reference to the first class. A third class of suitable transfer media includes an adhesive mixture of vinyl monomers or monomers and polymers, the polymerization of which is initiated with a catalyst such as benzoyl peroxide and with or without added amine accelerators, which when heated produces a mass such as characterized above with reference to the first class. A fourth class of suitable transfer media includes a solvent which does not attack the tape but which softens and dissolves the surface stratum of a plastic microscope slide producing an adhesive semi-fluid layer which, when the solvent is diffused therefrom, forms a mass similar to that described above with reference to the first class but in which the mass is in fact an integral surface portion of the slide.

An example of a transfer medium of the second class comprises a photopolymerizable adhesive mixture comprising 100 pts. (wt.) cycloxexyl methacrylate, two pts. (wt., benzoin ethyl ether, and three pts. (wt.) dimethyl aniline. This mixture was applied in an approximately 0.001 inch thick layer between a smear on a Mylar tape surface and a glass slide and was polymerized in five minutes by irradiation at a distance of one inch from the laminate by a 4 watt GE F4T5 ultraviolet lamp.

An example of a transfer medium of the third class comprises a thermally polymerizable adhesive mixture consisting of 130 pts. (wt.) polyester-styrene solution sold as Duro brand resin for bonding glass fibers, and 1 pt. (wt.) methyl ethyl ketone peroxide catalyst mixture sold as Duro brand liquid hardener. This mixture was applied in a layer of approximately 0.001 inch between the smear on a Mylar tape surface and a glass slide and was polymerized in 5 minutes by heating at 60° C.

An example of a tranfer medium of the fourth class consists of a solute comprising a solvent of ethylene dichloride for a surface stratum of an acrylic slide structured of Lucite which solvent does not attack a tape structured of Mylar. This solvent was found to soften the appropriate portion of the surface stratum of the slide to at least a tacky semi-fluid state when applied in a layer less than 0.001 inch between a smear on such tape and such slide. The diffusion of the solvent, which was largely into the slide, was enhanced by exposure to heat at 60° C. over a period of 30 minutes.

In the form of FIG. 1, a lamp assembly spaced above the platen 18 for irradiation of the latter is indicated at 44. It is to be understood that the assembly 44 is provided as a source of heat or ultraviolet light for curing those types of transfer media requiring or enhanced by such treatment, and may be eliminated, together with the platen 18, where such treatment is not helpful in the use of the selected transfer medium. It will be apparent that while each laminate, comprising a portion of the tape 10, a smear 14 on the tape and a slide 25 overlying the smear with the transfer medium 40 against the underside of the slide (FIG. 4), travels over the platen 18 on the advance of the tape, the transfer medium, having a greater affinity for the slide than to the tape, is cured and firmly affixed with the smear to the slide in a manner to transfer the smear to the slide.

Each such laminate including a tape portion leaving the platen 18 is directed by the tape 10 over the idler roller 20 which bends the tape delaminating it from the slide as the tape passes to the collection spool 22. Such delaminating shown in FIG. 1 may be facilitated by eventual engagement of the underside of each slide 25 with an edge of a chute 46 directing the slides one after another to a suitable nonillustrated collection container. A transferred smear permeated and encapsulated in the above-described manner is indicated at 48 in FIG. 6. Such a transferred smear, permanently mounted to a slide, is in condition for examination under a microscope. While not shown or described heretofore, it will be apparent to those versed in the art that any convenient identification system may be employed to identify the donor or origin of each such transferred smear. It is also to be understood that the smear transfer technique of the invention is not limited to the specific physical and chemical properties of the smear-carrying substrate and the smear-receiving element or elements described herein.

While several forms of the apparatus and method for transferring a biological smear have been described, it will be apparent, especially to those versed in the art, that such apparatus and method may take other forms and are susceptible to various changes in details without departing from the principles of the invention.

What is claimed is:

1. Transfer apparatus for transferring a plurality of discrete biological cellular smears of blood from a substrate to a backing element, comprising:
   (a) substrate element having a first surface,
   (b) a plurality of smears of biological cellular material,
   (c) said biological cellular smears being positioned on said first surface of said substrate element in spaced relationship,
   (d) means adapted and constructed to move said substrate element along a predetermined path,
   (e) a plurality of backing elements each having a first surface,
   (f) supply means for said backing elements,
   (g) means adapted and constructed to move said backing element in proximity to said path and in opposing surface relationship with said first surface of said substrate element,
   (h) transfer medium,
   (i) said transfer medium being transparent and exhibiting a refractive index substantially that of said smear of biological cellular material,
   (j) means adapted and constructed when said transfer apparatus is operated to introduce along said path said transfer medium between the first surface of said backing element and the first surface of said substrate element in sufficient quantity to essentially encapsulate said smears of biological cellular material,
   (k) means adapted and constructed when said transfer apparatus is operated to sandwich said transfer medium between said first surface of said substrate element and said first surface of said backing element along said path whereby said smears of biological cellular material are encapsulated within said transfer medium,
   (l) means adapted and constructed when said transfer apparatus is operated to part said backing element from said substrate element along said path,
   (m) said transfer medium having sufficient adhesive properties whereby said transfer medium is selectively adhered to said first surface of said backing element and said smears of biological cellular matrial adhere to said transfer medium when said transfer apparatus is operated.

2. Transfer apparatus as defined in claim 1 wherein said smear of biological cellular material comprises a smear of blood.

3. Transfer apparatus as defined in claim 2 wherein said transfer medium is a liquid adhesive.

4. Transfer apparatus as defined in claim 3 wherein said substrate element is an elongated flexible element and said backing element is substantially rigid.

5. Transfer appparatus as defined in claim 4 wherein the transfer medium is hardenable and means is provided for hardening said transfer medium.

6. Transfer apparatus as defined in claim 5 wherein said transfer medium comprises a thermally polymerizable material.

7. Transfer apparatus as defined in claim 5 wherein said transfer medium comprises a photopolymerizable material.